United States Patent
Sakai et al.

(10) Patent No.: US 6,919,365 B2
(45) Date of Patent: Jul. 19, 2005

(54) IMIDAZOLIDINEDIONE DERIVATIVES AND USE THEREOF AS DRUGS

(75) Inventors: Yusuke Sakai, Kobe (JP); Jun Inoue, Kobe (JP)

(73) Assignee: Senju Pharmaceutical Co., Ltd., Osaka (JP)

(*) Notice: Subject to any disclaimer, the term of this patent is extended or adjusted under 35 U.S.C. 154(b) by 111 days.

(21) Appl. No.: 10/473,889

(22) PCT Filed: Apr. 8, 2002

(86) PCT No.: PCT/JP02/03509

§ 371 (c)(1),
(2), (4) Date: Oct. 2, 2003

(87) PCT Pub. No.: WO02/083649

PCT Pub. Date: Oct. 24, 2002

(65) Prior Publication Data

US 2004/0110811 A1 Jun. 10, 2004

(30) Foreign Application Priority Data

Apr. 11, 2001 (JP) .................................. 2001-112373

(51) Int. Cl.⁷ .................. A61K 31/4166; C07D 233/74
(52) U.S. Cl. .................. 514/389; 514/390; 548/317.1; 548/318.5
(58) Field of Search .................. 548/317.1, 318.5; 514/389, 390

(56) References Cited

U.S. PATENT DOCUMENTS 5,223,523 A  6/1993  Adams, Jr. et al.

FOREIGN PATENT DOCUMENTS

EP  780125  6/1997
JP  9-31061  2/1997

OTHER PUBLICATIONS

Costanzo et al., Journal of Medicinal Chemistry, 46, 3865–3876, 2003.*
Fukami et al., Current Pharmaceutical Design, 4, 439–453, 1998.*
Rice et al., Current Pharmaceutical Design, 4, 381–396, 1998.*
Takai et al., Current Vascular Pharmacology, 1, 217–224, 2003.*
Niwata et al., Journal of Medicinal Chemistry, 40, 2156–2163, 1997.*

* cited by examiner

Primary Examiner—Fiona T. Powers
(74) Attorney, Agent, or Firm—Wenderoth, Lind & Ponack, L.L.P.

(57) ABSTRACT

The present invention is to provide an imidazolidinedione derivative and oxazolidinedione derivative represented by the following general Formula (I) having the chymase and/or tryptase inhibition activity

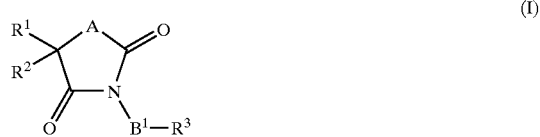

[wherein $R^1$ and $R^2$ are the same or different, and denote a lower alkyl group or a phenyl group, or $R^1$ and $R^2$ are taken together to form a ring, $R^3$ denotes an optionally substituted naphthyl group or heterocyclic group, A denotes oxygen or $NR^4$ ($R^4$ is hydrogen or optionally substituted lower alkyl group), or $NB^2R^5$ ($R^5$ is aryl group, and $B^2$ is carbonyl group or sulfonyl group), and $B^1$ denotes a carbonyl group or a sulfonyl group], or a pharmaceutically acceptable salt thereof.

11 Claims, No Drawings

IMIDAZOLIDINEDIONE DERIVATIVES AND USE THEREOF AS DRUGS

This application is a U.S. national stage of International Application No. PCT/JP02/03509 filed Apr. 8, 2002.

TECHNICAL FIELD

The present invention relates to an imidazolidinedione derivative or oxazolidinedione derivative or a pharmaceutically acceptable salt thereof, and a medicament containing these. These compounds have the chymase and/or tryptase inhibition activity, and are useful for preventing or treating various diseases associated with chymase and/or tryptase.

BACKGROUND ART

Chymase is one of neutral serine proteases (about 30 kD), and since it is an enzyme which converts angiotensin I into angiotensin II in tissues [J. Biol. Chem., vol.265, pp.22348 (1990)], it is said to be associated with induction of cardiac or circulatory diseases caused by angiotensin II. In addition, since chymase has been revealed to have the activity of promoting activation from collagenase to active collagenase, limitative degradation of extracellular matrix, thrombin or IgG, and release of histamine from mast cells, it is thought that chymase is also involved in allergic or inflammatory diseases. Further, although the action of chymase in the ocular tissue has not been completely elucidated, it is thought to be involved in regulating ophthalmic circulation (ophthalmic blood stream, aqueous humor circulation) and ciliary muscle. From the aforementioned wide activities of chymase in a living body, it is expected that an agent which inhibits such the enzyme is useful as an agent for preventing and treating various diseases.

As a chymase inhibiting agent, there have been previously known an imidazolidine derivative [(WO 96/04248 (counterparts: EP721944, U.S. Pat. No. 5,691,335)], an acetamide derivative [WO 98/09949 (counterpart: EP936216)], a triazinesulfone derivative (JP-H10-245384 A), a thiazolidine derivative (JP-2000-95770 A, JP-2000-103785 A), a quinazoline derivative (WO 97/11941), a phenolester derivative (JP-H10-87567A), a thiazine derivative (EP 0713876), a heterocyclic amide compound [WO 96/33974 (counterpart: EP826671, U.S. Pat. No. 5,948,785), WO 98/18794 (counterpart: EP940400, U.S. Pat. No. 6,080,738)], a peptide compound [Proc. Natl. Acad. Sci. U.S.A., vol.92, pp6738 (1995)], a hydantoin derivative (JP-H09-31061A), and so on. However, these compounds have not been put into practice yet.

Tryptase, like chymase, belongs to a serine protease family, and is isolated and purified from human lung as a protease having the trypsin-like substrate specificity [J. Biol. Chem, vol. 259, pp11046, (1984)]. Tryptase is present mainly in mast cells, and is also present in lymphocyte and bronchial mucous secreting cells, and is characterized in that, even after released to outside cells, the activity is sufficiently maintained in plasma or extracellular space. In mast cells, a majority of tryptase is stored in secretory granules and, when cells are activated, tryptase together with other enzymes (peroxidase, chymase etc.) and chemical mediators (e.g. histamine. leukotrienes, prostaglandins) is released by degranulation [N. Engl. J. Med., vol. 316, pp1622 (1987)].

Tryptase is related to a variety of diseases. For example, since tryptase increases the contractility of airway smooth muscle by inactivating a vasoactive intestinal peptide having the broncodilatory activity, it is said to be one cause for asthma [J. Pharmacol. Exp. Ther., vol. 244, pp133 (1988)]. In addition, tryptase has been shown to promote cell proliferation of fibroblast, and is said to be involved in interstitial pneumonia, pulmonary fibrosis, hepatic fibrosis, hepatic cirrhosis and pterygium [J. Clin. Invest., vol. 88, pp493 (1991), J Jpn Ophthalmol Soc, vol. 101, pp662 (1997)]. In addition, since tryptase activates prostoromelisin to cause activation of collagenase, and initiate destruction of cartilage and periodontal connecting tissue, tryptase may be a cause for arthritis or periodontal disease, and may be involved in other various tissue inflammations and re-building. Further, since tryptase cleaves a calcitonin gene-related peptides, it is involved in neurogenic inflammation [Am. J. Respir. Cell Mol. Biol., vol. 4, pp387 (1991)]. Tryptase promotes blood coagulation disorder by inactivating the coagulation precursor function of high-molecular kininogen, and degrading fibrinogen. Viruses having an outer membrane glycoprotein such as influenza and Sendai viruses are fused with a target cell membrane by degradation of the glycoprotein by tryptase and invade the cells. Examples of the virus include parainfluenza viruses, RS viruses, measles viruses and mumps viruses. As a tryptase inhibiting agent, natural leupeptin and antipain and some benzamidine derivatives are known [Biol. Chem. Hoppe-Seyler, vol.369, pp617 (1988)]. Besides, there are known an aminohexanoyl derivative (JP 2000-302675A), a polyfluoroalkylated tripeptide derivative [JP-H05-112598 A (counterparts: EP503203, U.S. Pat. Nos. 5,391,705, 5,498,779, 5,563,156)], a peptide derivative [JP-H08-507768 A (counterpart: EP688337)], a secretory leukocyte protease inhibitor (JP-10-505833 A), a leech-derived polypeptide [JP-H09-500532 A (counterparts: EP714408, U.S. Pat. No. 5,972,698)], a guanidine derivative (JP-Re 97/037969 A), antileukoprotease (JP-Re 95/025539 A), associated peptides (JP Re97/003694-A), and so on. However, these compounds have not been put into practice yet.

OBJECT OF THE INVENTION

An object of the present invention is to provide a novel imidazolidinedione derivative and oxazolidinedione derivative having the excellent chymase and/or tryptase inhibiting activity.

DISCLOSURE OF THE INVENTION

The present inventors studied intensively and, as a result, generated an imidazolinedione derivative and an oxazolidinedione derivative having the excellent chymase and/or tryptase inhibition activity, and further researched, which resulted in completion of the present invention.

That is, the present invention relates to:

(1) a compound represented by the general formula (I):

[wherein $R^1$ and $R^2$ are the same or different, and denote a lower alkyl group or a phenyl group, or $R^1$ and $R^2$ are taken together to form a ring, $R^3$ denotes an optionally substituted naphthyl group or heterocyclic group, A denotes oxygen or $NR^4$ ($R^4$ is hydrogen or optionally substituted lower alkyl group), or $NB^2R^5$ ($R^5$ is aryl group, and $B^2$ is carbonyl group or sulfonyl group), and $B^1$ denotes a carbonyl group or a sulfonyl group], or a pharmaceutically acceptable salt thereof, (2) the compound according to the (1), wherein $R^1$ and $R^2$ are the same or different, and are a lower alkyl group or a phenyl group, $R^3$ is a furyl group or an optionally substituted naphthyl group, and A is oxygen or $NR^4$ ($R^4$ is hydrogen or optionally substituted lower alkyl group) in the general formula (I), or a pharmaceutically acceptable salt thereof, (3) the compound according to the (1), wherein $B^1$ and $B^2$ are a carbonyl group in the general formula (I), or a pharmaceutically acceptable salt thereof, (4) a medicament, which comprises the compound described in any one of the (1) to (3), or a pharmaceutically acceptable salt thereof, (5) a chymase and/or tryptase inhibiting agent, which comprises the compound described in any one of the (1) to (3), or a pharmaceutically acceptable salt thereof, (6) the medicament described in the (4), which is an agent for preventing or treating diseases associated with chymase and/or tryptase, (7) the medicament described in the (6), wherein the disease associated with chymase and/or tryptase is allergic, inflammatory or circulatory disease, (8) the medicament described in the (6), wherein the disease associated with chymase is chorioretinopathy, glaucoma, myopia or asthenopia, (9) a pharmaceutical composition, which comprises the compound described in any one of the (1) to (3), or a pharmaceutically acceptable salt thereof,

(10) a method of preventing or treating diseases associated with chymase and/or tryptase, which comprises administering an effective amount of the compound described in any one of the (1) to (3), or a pharmaceutically acceptable salt thereof to a warm-blooded animal,

(11) a use of the compound described in any one of (1) to (3), or pharmaceutically acceptable salt thereof for manufacturing a chymase and/or tryptase inhibiting agent.

DETAILED DESCRIPTION OF THE INVENTION

In the compound represented by the general formula (I) of the present invention, a lower alkyl group represented by $R^1$ and $R^2$ refers to a straight or branched alkyl group having a carbon number of 1 to 5, such as a methyl group, an ethyl group, a propyl group, an isopropyl group, a butyl group, a sec-butyl group, a tert-butyl group, a pentyl group, an isopentyl group, a neopentyl group and a tert-pentyl group, particularly preferably a methyl group.

In addition, examples of a ring which $R^1$ and $R^2$ may be taken together to form include a ring having a carbon number of 3 to 7, such as cyclopropane, cyclobutane, cyclopentane, cyclohexane and cycloheptane. Preferably, the ring is cyclohexane.

A heterocyclic group represented by $R^3$ is a 5-membered or 6-membered compound containing at least one of an oxygen atom, a sulfur atom and a nitrogen atom, such as a furyl group, a thienyl group, a pyrrolyl group and a pyridyl group, preferably a furyl group. In addition, a naphthyl group and a heterocyclic group represented by $R^3$ may have a substituent such as a carboxyl group.

A lower alkyl group of $R^4$ represented by $NR^4$ in A has the same meaning as that of a lower alkyl group represented by $R^1$ and $R^2$, and examples of a substituent include a phenyl group and a benzoyl group which may have a substituent, and a carboxyl group optionally esterified with a lower alkyl group. Examples of a substituent of a phenyl group include a halogen (e.g. chlorine, fluorine, bromine etc.), a cyano group, and so on. Examples of a substituent of a benzoyl group include lower alkyl groups having a carbon number of 1 to 3 (methyl group, ethyl group, propyl group, isopropyl group) and lower alkoxy groups (methoxy group, ethoxy group, propoxy group, isopropoxy group). As a lower alkyl group, a methyl group is preferable. As a lower alkoxy group, a methoxy group is preferable.

Examples of an aryl group of $R^5$ represented by $NB^2R^5$ in A include a phenyl group, a naphthyl group and a 2-naphthyl group, preferably a naphthyl group and a 2-naphthyl group. As a carbonyl group and a sulfonyl group represented by $B^1$ and $B^2$, a carbonyl group is more preferable.

The compound represented by the general formula (I) of the present invention can be prepared by the following preparing method, or by a similar method.

i) Case where A is oxygen:

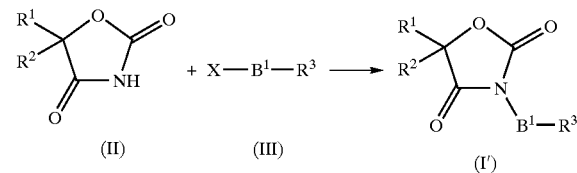

[wherein $R^1$, $R^2$, $R^3$ and $B^1$ are as defined above, and X denotes halogen atom (chlorine, bromine, fluorine, iodine etc.)]

A compound of the general formula (I') in which A in the compound represented by the general formula (I) is oxygen, can be prepared by reacting 5,5-di-substituted oxazolidin-2,4-dione represented by the formula (II) or a salt thereof with an acid halide derivative represented by the formula (III), and performing the conventional purification such as recrystallization, column chromatography and the like.

Such the reaction can be carried out in a reaction solvent in the presence or absence of an inorganic base or an organic base. Examples of a reaction solvent which can be used in the present reaction include the conventional solvents which do not have adverse influence on a reaction, such as methylene chloride, chloroform, N,N-dimethylformamide, benzene, toluene, ethylbenzene, cyclohexane, hexane, heptane, diethyl ether, tetrahydrofuran and the like, and a mixed solvent thereof, preferably N,N-dimethylformamide and tetrahydrofuran.

An inorganic base used in the present reaction include alkali metal hydrides such as sodium hydride and the like, alkali metal carbonates such as potassium carbonate, and alkali metal bicarbonates such as sodium bicarbonate. Examples of an organic base include trialkylamine such as triethylamine, diisopropylethylamine and the like, pyridine, lutidine, picoline, 4-dimethylaminopyridine, 1,8-diazabicyclo[5.4.0]undec-7-ene (DBU), 1,5-diazabicyclo[4.3.0]non-5-ene (DBN) and the like. Sodium hydride and potassium carbonate are preferable. Such the base is preferably used in a range of 0.1 to 2.0 molar ratio relative to 1 mol of 5,5-di-substituted oxazolidine-2,4-dione represented by the formula (II) or a salt thereof. A reaction temperature is usually in a range of under cooling to under warming, preferably in a range of −10° C. to 30° C.

ii) Case where A is NR⁴ or NB²R⁵:

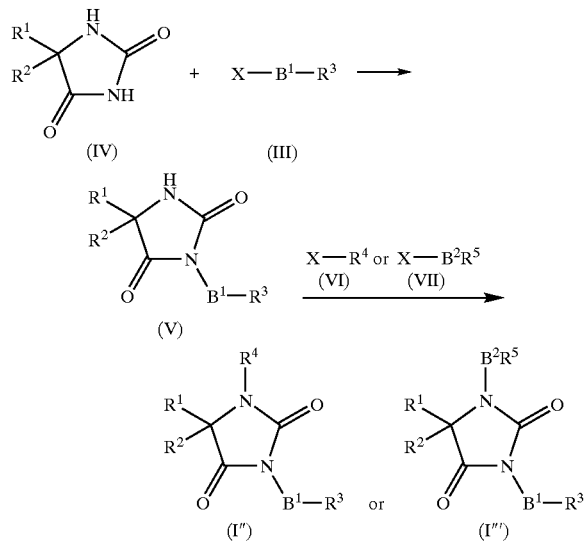

[wherein respective symbols are as defined above]

A compound of the formula (V) in which A in the compound represented by the general formula (I) is NR⁴(R⁴ is hydrogen), can be prepared by reacting 5,5-di-substituted imidazolidine-2,4-dione represented by the formula (IV) or a salt thereof with an acid halide derivative represented by the formula (III) under the same conditions as those for the i), and performing the conventional purification such as recrystallization, column chromatography and the like. Further, a compound of the formula (I") or (I'") in which A in the compound represented by the general formula (I) is denoted by NR⁴ or NB²R⁵, can be prepared by reacting with an alkyl halide derivative (VI) or an acid halide derivative (VII), and performing the conventional purification procedure such as recrystallization, column chromatography and the like. The reaction can be carried out by using an alkyl halide derivative or an acid halide derivative in a range of a molar ratio of 0.5 to 2.0, preferably a molar ratio of 0.9 to 1.2 relative to the compound represented by the formula (V) under the same other reaction conditions as those for the i).

When the acid halide derivative (VII) and the compound represented by the formula (III) are the same, the compound of the formula (I'") can be easily obtained by performing a reaction by adding the compound represented by the formula (III) at a molar ratio of 2 to 2.2 relative to 1 mol of the compound represented by the formula (IV).

Examples of preferable compounds of the present invention are as follows:

(1) 3-(2-Naphthylcarbonyl)-5,5-diphenylimidazolidine-2,4-dione,
(2) 3-Naphthylcarbonyl-5,5-diphenylimidazolidine-2,4-dione,
(3) Ethyl 2-(3-naphthylcarbonyl-2,4-dioxo-5,5-diphenylimidazolidinyl)acetate,
(4) tert-Butyl 2-(3-naphthylcarbonyl-2,4-dioxo-5,5-diphenylimidazolidinyl)acetate,
(5) 3-Naphtylcarbonyl-2,4-dioxo-5,5-diphenylimidazolidinylacetic acid,
(6) 4-((2,5-Dioxo-4,4-diphenylimidazolidinyl)carbonyl) naphthalenecarboxylic acid,
(7) 5-Methyl-3-naphthylcarbonyl-5-phenylimidazolidine-2,4-dione,
(8) 5,5-Dimethyl-3-naphthylcarbonyl imidazolidine-2,4-dione,
(9) 5,5-Dimethyl-3-naphthylcarbonyl-1,3-oxazolidine-2,4-dione,
(10) 3-(2-Furylcarbonyl)-5,5-diphenylimidazolidine-2,4-dione,
(11) 3-(2-Naphthylsulfonyl)-5,5-diphenylimidazolidine-2,4-dione,
(12) 3-Naphthylsulfonyl-5,5-diphenylimidazolidine-2,4-dione,
(13) tert-Butyl (5,5-dimethyl-3-naphthylcarbonyl-2,4-dioxoimidazolidinyl)acetate,
(14) tert-Butyl (5-methyl-3-naphthylcarbonyl-2,4-dioxo-5-phenylimidazolidinyl)acetate,
(15) 5,5-Dimethyl-3-naphthylcarbonyl-2,4-dioxoimidazolidinylacetic acid,
(16) 5-Methyl-3-naphthylcarbonyl-2,4-dioxo-5-phenylimidazolidinylacetic acid,
(17) 5,5-Dimethyl-3-(2-naphthylsulfonyl)imidazolidine-2,4-dione,
(18) 5,5-Dimethyl-3-naphthylsulfonylimidazolidine-2,4-dione,
(19) 5-Methyl-3-(2-naphthylsulfonyl)-5-phenylimidazolidine-2,4-dione,
(20) 1-Benzyl-3-naphthylcarbonyl-5,5-diphenylimidazolidine-2,4-dione,
(21) 3-Naphthylcarbonyl-1-(2-oxo-2-phenylethyl)-5,5-diphenylimidazolidine-2,4-dione,
(22) 1-Methyl-3-naphthylcarbonyl-5,5-diphenylimidazolidine-2,4-dione,
(23) 1-Isobutyl-3-naphthylcarbonyl-5,5-diphenylimidazolidine-2,4-dione,
(24) 1-(4-Fluorobenzyl)-5-methyl-3-naphthylcarobnyl-5-phenylimidazolidine-2,4-dione,
(25) 1-(3-Chlorobenzyl)-5-methyl-3-naphthylcarbonyl-5-phenylimidazolidine-2,4-dione,
(26) 5-Methyl-3-naphthylcarbonyl-1-(2-oxo-2-phenylethyl)-5-phenylimidazolidine-2,4-dione
(27) 4-(5,5-Dimethyl-3-naphthylcarbonyl-2,4-dioxoimidazolidinylmethyl)benzonitrile,
(28) 1-(3-Chlorobenzyl)-5,5-dimethyl-3-naphthylcarbonylimidazolidine-2,4-dione,
(29) 1-(4-Chlorobenzyl)-5,5-dimethyl-3-naphthylcarbonylimidazolidine-2,4-dione,
(30) 5,5-Dimethyl-3-naphthylcarbonyl-1-(2-oxo-2-phenylethyl)imidazolidine-2,4-dione,
(31) 5,5-Dimethyl-3-naphthylcarbonyl-1-(2-oxo-2-p-tolylethyl)imidazolidine-2,4-dione,
(32) 1-(2-(4-Methoxyphenyl)-2-oxoethyl)-5,5-dimethyl-3-naphthylcarbonylimidazolidine-2,4-dione,
(33) 5,5-Dimethyl-1,3-bisnaphthylcarbonylimidazolidine-2,4-dione,
(34) 3-Naphthylcarbonyl-1,3-diazaspiro[4,5]decane-2,4-dione,
(35) 5,5-Dimethyl-1,3-bis-(2-naphthylsulfonyl)imidazolidine-2,4-dione,
(36) 5,5-Dimethyl-1,3-bisnaphthylsulfonylimidazolidine-2,4-dione,
(37) 5-Methyl-1,3-bis-(2-naphthylsulfonyl)-5-phenylimidazolidine-2,4-dione.

Examples of a pharmaceutically acceptable salt of the compound represented by general formula (I) of the present invention include alkali metal salts such as a sodium salt and a potassium salt, alkaline earth metal salts such as a calcium salt and a magnesium salt, salts with inorganic acids such as hydrochloride, hydrobromide, sulfate, nitrate and phosphate, and salts with organic acids such as acetate, citrate, and toluenesulfonate, being not limiting.

In addition, the present invention includes various solvates and crystal polymorphisms of the compound represented by the general formula (I), and prodrugs thereof The compound represented by the general formula (I) of the present invention and a pharmaceutically acceptable salt thereof (hereinafter, referred to as the present compound in some cases) are novel compounds which have not described in literatures yet and, since they have the excellent chymase and/or tryptase inhibition activity as shown in Experimental Example described later, they are useful as a medicament as a chymase and/or tryptase inhibiting agent containing them as an active ingredient by combining with a carrier described later as necessary.

Since the present compound has the chymase and/or tryptase inhibition activity, the compound is useful for preventing or treating diseases associated with chymase and/or tryptase, of a warm-blooded animal (mammals such as human, monkey, dog, cat, rabbit, guinea pig, rat, hamster and mouse, birds such as chicken, pigeon, turkey).

For example, by the chymase and tryptase inhibition activity, the present compound can be used as an agent for preventing or treating systemic or local inflammatory or allergic diseases (e.g. digestive tract inflammatories such as pancreatitis, ulcerative colitis and Crohn's disease, and nephritis, hepatitis, bronchopneumonia, atopy, arthritis and rheumatism as systemic disease, keratoconjunctivitis, iridocyclitis, uveitis, orbital inflammation, vernal catarrh, allergic rhinitis), or as an agent for preventing or treating restenosis after circulatory diseases (eg. hypertension, arterial sclerosis, cardiac infarct, hypercardia, heart failure), restenosis after blood vessel disorder due to percutaneous transluminal angioplasty, diabetic and non-diabetic renal disorder, and peripheral circulatory disorder, or as an agent for preventing or treating itching associated with inflammatory or allergic disorders. By the chymase inhibition activity, the present compound can be used as an agent for preventing or treating ophthalmic circulatory damaging diseases (chorioretinopathy; retinitis pigmentosa, macular degeneration, ischemic optic nerve disease, arteriovenous occulusion, diabetic retinopathy, choroidal disease following retinal lesion) and glaucoma. In addition, since the present compound has ciliary muscle relaxing activity of contracting, it can be used for improving myopia or asthenopia. In addition, by the tryptase inhibition activity, the present compound can be used as an agent for preventing or treating blood coagulation disorder such as thrombophlebitis and disseminated intravascular coagulation, psoriasis, dermal diseases such as scleroderma and virus diseases, as well as interstitial pneumonia, pulmonary fibrosis, hepatic cirrhosis, periodontal diseases and pterygium.

For the aforementioned prevention and treatment, the present compound can be appropriately applied orally or parenterally. Examples of the form of the preparation include solid preparations such as tablets, granules, powders, capsules, ointments and the like and liquid preparations such as injectables, eye drops, nasal drops and the like. Any preparations can be appropriately prepared by the known method. In these preparations, normally used excipients (starch, glucose, fructose, sucrose, calcium phosphate etc.), binders (starch, gum arabic, gelatin solution, sodium arginate, carmerose solution etc.), disintegrating agents (starch, potassium carbonate, crystalline cellulose etc.), lubricants (stearic acid, magnesium stearate, talc etc.), absorption promoters (thioglycolic acid, capric acid, caprylic acid etc.), buffers (boric acid, borax, sodium acetate, citrate buffer, phosphate buffer etc.), surfactants (sodium laurylsulfate, Polysorbate 80, polyoxyethylene hydrogenated castor oil etc.), solubilizers (sodium laurylsulfate, sodium benzoate, ethylenediamine, potassium iodide etc.), preservatives (benzalkonium chloride, parabens, chlorobutanol etc.), emulsifiers (gum arabic, tragacanth, gelatin, polyvinylpyrrolidone etc.), isotonics (sodium chloride, glycerin, mannitol etc.), stabilizers (sodium edetate, sodium pyrosulfite etc.), pH adjusting agents (hydrochloric acid, citric acid, sodium hydroxide etc.) and the like may be appropriately used.

When the present compound is used, for example, as an agent for preventing or treating circulatory diseases, a dose varies depending on a kind of a subject disease, a kind of a compound to be used, an age, a weight and symptom of a patient and its dosage form and, for example in the case of an internal preparation, the present compound may be administered to an adult patient a few times per day at a one time amount of 1 mg to 100 mg, more preferably 5 mg to 25 mg. In addition, in the case of an intravenous injectable, the present compound may be administered to the same patient once per day at 0.1 mg to 25 mg, more preferably 0.5 to 5 mg. Further, when locally administered to a patient with local inflammatory disease, an eye drops, a nasal drop or an ointment containing the present compound at 0.01 w/v % to 2.0 w/v %, preferably 0.05 w/v % to 0.5 w/v % is dropped to eyes, dropped to noses or coated at 1 to a few drops or an appropriate amount per once, once to 8 times per day.

The present compound may be used by appropriately combining two or more kinds depending on the purpose and the necessity. In addition, as far as it is not contrary to the object of the present invention, the present compound may be used by appropriately combining with chymase and/or tryptase inhibiting ingredients which are not included in the present invention, other ingredients having the same drug efficacy as that of the present invention, and other effective ingredients.

BEST MODE FOR CARRYING OUT THE INVENTION

The present invention will be explained in more detail by the following Examples and Experimental Examples, but the present invention is not limited by them at all.

In physical property values of the compounds described in Examples, nuclear magnetic resonance spectrum (NMR) was measured using Varian Gemini 2000.

EXAMPLE 1

3-(2-Naphthylcarbonyl)-5,5-diphenylimidazolidine-2,4-dione (Compound 1)

0.5 g of 5,5-diphenylimidazolidine-2,4-dione was dissolved in tetrahydrofuran (5 mL), and sodium hydride (60%, in oil) (87 mg) was added at 0° C. under ice-cooling. After stirred for 30 minutes, 2-naphthoyl chloride (415 mg) was added at 0° C., followed by stirring at room temperature for 2.5 hours. After water was carefully added, ethyl acetate (200 mL) was added, and the layers were separated. The resulting organic layer was washed with a saturated brine, and dried over anhydrous magnesium sulfate, and the solvent was distilled off. Further purification by silica gel chromatography (hexane:ethyl acetate=3:1) afforded white crystals. The resulting fraction was recrystallized from isopropyl ether (IPE) to obtain 441 mg of white crystals.

$^1$H-NMR (CDCl$_3$) δ7.25 (1H, brs), 7.38–7.48 (10H, m), 7.54 (1H, ddd, J=8.1, 6.9, 1.2 Hz), 7.63 (1H, ddd, J=8.3, 6.9, 1.4 Hz), 7.79–7.89 (4H, m), 8.26 (1H, d, J=1.2 Hz).

$^{13}$C-NMR (CDCl$_3$) δ70.6, 125.0, 126.9, 127.1, 127.9, 128.7, 129.0, 129.1, 129.4, 129.8, 132.2, 133.0, 136.3, 138.4, 153.4, 165.9, 171.0.

EXAMPLE 2

3-Naphthylcarbonyl-5,5-diphenylimidazolidine-2,4-dione (Compound 2)

0.5 g of 5,5-diphenylimidazolidine-2,4-dione was dissolved in tetrahydrofuran (5 mL), and sodium hydride (60%, in oil) (87 mg) was added at 0° C. under ice-cooling. After stirred for 30 minutes, 1-naphthoyl chloride (396 mg) was added at 0° C., followed by stirring at room temperature for 2.5 hours. After water was added carefully, ethyl acetate (200 mL) was added, and the layers were separated. The resulting organic layer was washed with a saturated brine, and dried over anhydrous magnesium sulfate, and the solvent was distilled off. Further purification by silica gel chromatography (hexane: ethyl acetate=7:3) afforded 544 mg of white powder.

$^1$H-NMR (CDCl$_3$) δ6.95 (1H, brs), 7.36–7.42 (9H, m), 7.43 (1H, d, J=7.3 Hz), 7.46 (1H, d, J=7.2 Hz), 7.52–7.61 (2H, m), 7.71 (1H, dd, J=7.3, 1.2 Hz), 7.89–7.92 (1H, m), 8.06 (1H, d, J=8.2 Hz), 8.45–8.48 (1H, m).

$^{13}$C-NMR (CDCl$_3$) δ70.2, 124.4, 124.7, 126.9, 128.6, 128.8, 129.0, 129.0, 129.6, 130.2, 130.8, 133.7, 134.5, 138.4, 152.9, 165.8, 171.2.

EXAMPLE 3

Ethyl 2-(3-naphthylcarbonyl-2,4-dioxo-5,5-diphenylimidazolidinyl)acetate (Compound 3)

3-Naphthylcarbonyl-5,5-diphenylimidazolidine-2,4-dione (406 mg) was dissolved in dimethylformamide (DMF: 2 mL), ethyl bromoacetate (167 mg) was added, and potassium carbonate (138 mg) was further added. The reaction solution was stirred at room temperature overnight. After water was added carefully, ethyl acetate (100 mL) was added, followed by extraction. The resulting organic layer was washed with a saturated brine, and dried over anhydrous magnesium sulfate, and the solvent was distilled off. Recrystallization from methanol afforded 338 mg of white crystals.

$^1$H-NMR (CDCl$_3$) δ1.03 (3H, t, J=7.1 Hz), 3.79 (2H, q, J=7.1 Hz), 4.13 (2H, s), 7.26–7.62 (13H, m), 7.78 (1H, dd, J=7.1, 1.3 Hz), 7.89–7.92 (1H, m), 8.07 (1H, d, J=8.4 Hz), 8.46–8.49 (1H, m).

$^{13}$C-NMR (CDCl$_3$) δ13.9, 42.6, 61.5, 74.8, 124.4, 124.8, 126.8, 128.5, 128.8, 129.0, 129.4, 129.7, 130.1, 130.8, 133.7, 134.4, 136.2, 152.6, 165.7, 166.6, 170.7.

EXAMPLE 4 tert-Butyl 2-(3-naphthylcarbonyl-2,4-dioxo-5,5-diphenylimidazolidinyl)acetate (Compound 4)

3-Naphthylcarbonyl-5,5-diphenylimidazolidine-2,4-dione (879 mg) was dissolved in DMF (3 mL), tert-butyl bromoacetate (421 mg) was added, and potassium carbonate (299 mg) was further added. The reaction solution was stirred at room temperature overnight. After water was carefully added, ethyl acetate (200 mL) was added, followed by extraction. The resulting organic layer was washed with a saturated brine, and dried over anhydrous magnesium sulfate, and the solvent was distilled off. Further, recrystallization from methanol afforded 846 mg of white crystals.

$^1$H-NMR (CDCl$_3$) δ1.17 (9H, s), 4.05 (2H, s), 7.33–7.61 (13H, m), 7.78 (1H, dd, J=7.3, 1.2 Hz), 7.90 (1H, d, J=7.3, 2.3 Hz), 8.06 (1H, d, J=8.4 Hz), 8.45–8.48 (1H, m).

$^{13}$C-NMR (CDCl$_3$) δ27.7, 43.2, 74.8, 82.2, 124.4, 124.8, 126.8, 128.5, 128.6, 128.7, 128.9, 129.3, 129.8, 130.1, 130.8, 133.7, 134.3, 136.4, 152.5, 165.3, 165.7, 170.8.

EXAMPLE 5

3-Naphthylcarbonyl-2,4-dioxo-5,5-diphenylimidazolidinylacetic acid (Compound 5)

tert-Butyl 2-(3-naphthylcarbonyl-2,4-dioxo-5,5-diphenylimidazolidinyl)acetate (300 mg) was dissolved in a 20% trifluoroacetic acid/dichloromethane solution (2 mL), and the solution was stirred at room temperature overnight. After a 1N aqueous hydrogen chloride solution was added, the solution was extracted three times using chloroform (50 mL). The resulting organic layer was washed with a saturated brine, and dried over anhydrous magnesium sulfate, and the solvent was distilled off. Further, recrystallization from IPE afforded 231 mg of white crystals.

$^1$H-NMR (CDCl$_3$) δ4.11 (2H, s), 7.31–7.61 (13H, m), 7.74 (1H, dd, J=7.3, 1.2 Hz), 7.89–7.92 (1H, m), 8.06 (1H, d, J=8.4 Hz), 8.44–8.47 (1H, m).

$^{13}$C-NMR (CDCl$_3$) δ42.1, 74.9, 124.4, 124.7, 126.8, 128.4, 128.5, 128.8, 129.0, 129.6, 130.2, 130.7, 133.7, 134.5, 135.9, 152.6, 165.6, 170.6, 171.4.

EXAMPLE 6

4-((2,5-Dioxo-4,4-diphenylimidazolidinyl)carbonyl) naphthalenecarboxylic acid (Compound 6)

1,4-Naphthalenedicarboxylic acid (0.43 g) was dissolved in thionyl chloride (1.89 g), and the solution was stirred at room temperature for 3 hours. The solvent was distilled off under reduced pressure, and a suspension of a potassium salt (0.58 g) of 5,5-diphenylimidazolidine-2,4-dione in tetrahydrofuran (5 mL) was added to the residue. After stirred for 2 hours, water (20 mL) was added, ethyl acetate (200 mL) was further added, and the layers were separated. The resulting organic layer was washed with a saturated brine, and dried with anhydrous magnesium sulfate, and the solvent was distilled off Further silica gel chromatography with ethyl acetate afforded 244 mg of the pale yellow solid.

$^1$H-NMR (DMSO-d$_6$) δ7.34–7.48 (10H, m), 7.69 (1H, dd, J=3.4, 6.8 Hz), 7.74–7.86 (1H, m), 8.07–8.15 (2H, m), 8.78 (1H, dd, J=3.4, 6.8 Hz), 9.30 (1H, brs), 11.10 (1H, brs).

$^{13}$C-NMR (DMSO-d$_6$) δ70.3, 125.9, 126.1, 126.6, 126.9, 127.6, 127.9, 128.1, 128.2, 128.6, 128.9, 130.7, 132.3, 138.8, 139.9, 156.0, 168.5, 174.9.

EXAMPLE 7

5-(Methyl-3-naphthylcarbonyl-5-phenylimidazolidine-2,4-dione (Compound 7)

5-Methyl-5-phenylimidazolidine-2,4-dione potassium salt (228 mg) was suspended in tetrahydrofuran (5 mL), 1-naphthoyl chloride (188 mg) was added, and the mixture was stirred at room temperature overnight. To the reaction solution was added ethyl acetate (20 mL), and the mixture was filtered with a membrane filter (0.25 μm). After the solvent was distilled off, 364 mg of the resulting organic layer was purified by silica gel chromatography (hexane:ethyl acetate=2:1). Further recrystallization from ethyl acetate/IPE afforded 134 mg of white crystals.

$^1$H-NMR (CDCl$_3$) δ1.86 (3H, s), 6.20 (1H, brs), 7.34–7.45 (5H, m), 7.49–7.59 (5H, m), 7.65 (1H, dd, J=7.2, 1.2 Hz), 7.86–7.90 (1H, m), 8.04 (1H, d, J=8.2 Hz), 8.40–8.44 (1H, m).

$^{13}$C-NMR (CDCl$_3$) δ25.7, 63.7, 124.3, 124.6, 125.2, 126.8, 128.5, 128.7, 128.8, 129.1, 129.6, 130.0, 130.7, 133.7, 134.4, 137.9, 153.1, 165.9, 172.5.

EXAMPLE 8

5,5- Dimethyl-3-naphthylcarbonylimidazolidine-2,4-dione (Compound 8)

5,5-Dimethylimidazolidine-2,4-dione potassium salt (1.47 g) was suspended in tetrahydrofuran (5 mL), 1-naphthoyl chloride (1.46 g) was added, and the mixture was stirred at room temperature overnight. Ethyl acetate (50 mL) was added to the reaction solution, and the mixture was filtered with a membrane filter (0.25 μm). The resulting organic layer was purified by silica gel chromatography (hexane:ethyl acetate=1:1) to obtain 674 mg of white crystals.

$^1$H-NMR (CDCl$_3$) δ1.43 (6H, s), 6.62 (1H, brs), 7.48–7.66 (3H, m), 7.74 (1H, dd, J=7.3, 1.2 Hz), 7.92 (1H, d, J=7.8 Hz), 8.08 (1H, d, J=8.2 Hz), 8.48 (1H, d, J=8.2 Hz).

$^{13}$C-NMR (CDCl$_3$) δ25.2, 58.8, 124.4, 124.7, 126.8, 128.5, 128.8, 129.9, 130.8, 133.8, 134.3, 152.8, 166.2, 174.6.

EXAMPLE 9

5,5-Dimethyl-3-naphthylcarbonyl-1,3-oxazolidine-2,4-dione (Compound 9)

5,5-Dimethyl-2,4-oxazolidinedione potassium salt (84 mg) was suspended in tetrahydrofuran (1 mL), 1-naphthoyl chloride (95 mg) was added, and the mixture was stirred at room temperature overnight. To the reaction solution was added 4 mL of ethyl acetate, and the solution was filtered with a membrane filter (0.25 μm). The resulting organic layer was purified by silica gel chromatography (hexane:ethyl acetate=2:1), and further recrystallized from ethyl acetate/IPE to obtain 61 mg of white crystals.

$^1$H-NMR (CDCl$_3$) δ1.71 (6H, s), 7.52–7.71 (3H, m), 7.78 (1H, dd, J=7.3, 1.2 Hz2 Hz), 7.95 (1H, dd, J=8.8, 1.5 Hz), 8.14 (1H, d, J=8.2 Hz2 Hz), 8.57 (1H, dd, J=8.6, 1.0 Hz).

$^{13}$C-NMR (CDCl$_3$) δ23.8, 83.6, 124.3, 124.6, 127.1, 128.1, 128.9, 129.1, 130.8, 130.9, 133.9, 135.5, 150.4, 164.5, 173.3.

EXAMPLE 10

3-(2-Furylcarbonyl)-5,5-diphenylimidazolidine-2,4-dione (Compound 10)

5,5-Diphenylimidazolidine-2,4-dione (0.5 g) was dissolved in tetrahydrofuran (5 mL), and sodium hydride (60%, in oil) (87 mg) was added at 0° C. under ice-cooling. After stirred for 30 minutes, 2-furoyl chloride (235 mg) was added 0° C., and the mixture was stirred at room temperature for 2.5 hours. After water was added carefully, ethyl acetate (200 mL) was added, and the layers were separated. The resulting organic layer was washed with a saturated brine, and dried over anhydrous magnesium sulfate, and the solvent was distilled off. Further purification by silica gel chromatography (hexane:ethyl acetate=2:1) afforded white powders. The resulting foam was recrystallized from IPE to obtain 273 mg of white crystals.

$^1$H-NMR (CDCl$_3$) δ6.59 (1H, dd, J=3.7, 1.7 Hz), 7.13 (1H, brs), 7.32 (1H, dd, J=3.7, 0.6 Hz), 7.37–7.45 (10H, m), 7.64 (1H, dd, J=1.7, 0.6 Hz).

$^{13}$C-NMR (CDCl$_3$) δ70.6, 113.3, 123.1, 126.9, 128.9, 129.0, 138.4, 146.6, 148.7, 152.8, 154.2, 170.5.

EXAMPLE 11

3-(2-Naphthylsulfonyl)-5,5-diphenylimidazolidine-2,4-dione (Compound 11)

5,5-Diphenylimidazolidine-2,4-dione (0.5 g) was dissolved in tetrahydrofuran (5 mL), and sodium hydride (60%, in oil) (87 mg) was added at 0° C. under ice-cooling. After stirred for 30 minutes, 2-naphthalenesulfonyl chloride (471 mg) was added at 0° C., and the mixture was stirred at room temperature overnight. After water was added carefully, ethyl acetate (100 mL) was added, and the layers were separated. The resulting organic layer was washed with a saturated brine, and dried over anhydrous magnesium sulfate, and the solvent was distilled off. Further purification by silica gel chromatography (hexane:ethyl acetate=3:1 to 2:1) afforded 320 mg of white powder.

$^1$H-NMR (CDCl$_3$) δ6.70 (1H, brs), 7.17–7.34 (10H, m), 7.62–7.74 (2H, m), 7.92–8.01 (3H, m), 8.05 (1H, dd, J=1.8, 8.6 Hz), 8.72 (1H, d, J=1.5 Hz).

$^{13}$C-NMR (CDCl$_3$) δ70.2, 122.3, 126.8, 127.9, 128.0, 128.9, 129.0, 129.7, 129.9, 130.0, 130.9, 131.8, 134.5, 135.9, 137.8, 150.7, 168.8.

EXAMPLE 12

3-Naphthylsulfonyl-5,5-diphenylimidazolidine-2,4-dione (Compound 12)

5,5-Diphenylimidazolidine-2,4-dione (0.5 g) was dissolved in tetrahydrofuran (5 mL), and sodium hydride (60%, in oil) (87 mg) was added at 0° C. under ice-cooling. After stirred for 30 minutes, 1-naphthalenesulfonyl chloride (471 mg) was added at 0° C., and the mixture was stirred at room temperature overnight. After water was added carefully, ethyl acetate (100 mL) was added, and the layers were separated. The resulting organic layer was washed with a saturated brine, and dried over anhydrous magnesium sulfate, and the solvent was distilled off. The material was dissolved in ethyl acetate, and purified by silica gel chromatography (hexane:ethyl acetate=3:1 to 2:1) to obtain 100 mg of white powder.

$^1$H-NMR (CDCl$_3$+CD$_3$OD) δ7.13–7.37 (9H, m), 7.49–7.64 (4H, m), 7.95 (1H, m), 8.17 (1H, m), 8.53 (1H, m), 8.64 (1H, m).

$^{13}$C-NMR (CDCl$_3$+CD$_3$OD) δ70.2, 123.3, 124.2, 127.0, 127.3, 128.5, 128.8, 129.4, 129.7, 132.2, 133.1, 134.0, 136.6, 138.2, 151.1, 169.8.

EXAMPLE 13

Tert-butyl (5,5-dimethyl-3-naphthylcarbonyl-2,4-dioxoimidazolidinyl)acetate (Compound 13)

5,5-Dimethyl-3-naphthylcarbonylimidazolidine-2,4-dione (686 mg) was dissolved in DMF (5 mL), and tert-butyl bromoacetate (473 mg) was added. Potassium carbonate (352 mg) was further added, and the mixture was stirred at room temperature overnight. After water was added carefully to the reaction solution, ethyl acetate (200 mL) was added, followed by extraction. The resulting organic layer was washed with 1N hydrochloric acid, an aqueous saturated sodium bicarbonate solution and a saturated brine in turn, and dried over anhydrous magnesium sulfate, and the solvent was distilled off. Further purification by silica gel chromatography (hexane:ethyl acetate=2:1) afforded white crystals. The resulting fraction was recrystallized from IPE to obtain 679 mg of white powders.

$^1$H-NMR (CDCl$_3$) δ1.48 (9H, s), 1.50 (6H, s), 3.93 (2H, s), 7.49–7.66 (3H, m), 7.78 (1H, dd, J=7.3, 1.2 Hz2 Hz), 7.91 (1H, dd, J=8.8, 1.5 Hz), 8.07 (1H, d, J=8.2 Hz2 Hz), 8.50 (1H, d, J=8.9 Hz).

$^{13}$C-NMR (CDCl$_3$) δ22.9, 23.1, 28.0, 41.5, 61.8, 124.3, 124.8, 126.7, 128.5, 128.7, 129.8, 129.9, 130.8, 133.8, 134.3, 151.9, 165.9, 167.0, 173.8.

EXAMPLE 14 tert-Butyl (5-methyl-3-naphthylcarbonyl-2,4-dioxo-5-phenylimidazolidinyl)acetate (Compound 14)

5-Methyl-3-naphthylcarbonyl-5-phenylimidazolidine-2,4-dione (800 mg) was dissolved in DMF (8 mL) and tert-butyl bromoacetate (452 mg) was added. Potassium carbonate (336 mg) was further added, and the mixture was stirred at room temperature overnight. After water was added carefully to the reaction solution, ethyl acetate (200 mL) was added, followed by extraction. The resulting organic layer was washed with 1N hydrochloric acid, an aqueous saturated sodium bicarbonate solution and a saturated brine in turn, and dried over anhydrous magnesium sulfate, and the solvent was distilled off. Further recrystallization with IPE afforded 704 mg of white crystals.

$^1$H-NMR (CDCl$_3$) δ1.44 (9H, s), 1.96 (3H, s), 3.46 (1H, d, J=17.7 Hz), 4.31 (1H, d, J=17.7 Hz), 7.38–7.63 (8H, m), 7.76 (1H, dd, J=7.3, 1.2 Hz2 Hz), 7.90 (1H, dd, J=7.7, 1.7 Hz), 8.06(1H, d, J=8.2 Hz), 8.45–8.48 (1H, m).

$^{13}$C-NMR (CDCl$_3$) δ21.1, 28.0, 42.7, 67.3, 82.7, 124.4, 124.8, 126.1, 126.7, 128.5, 128.7, 129.3, 129.4, 130.0, 130.8, 133.7, 134.3, 134.4, 136.1, 152.7, 165.8, 166.8, 171.8.

EXAMPLE 15

5,5-Dimethyl-3-(naphthylcarbonyl)-2,4-dioxoimidazolidinylacetic acid (Compound 15)

tert-Butyl (5,5-dimethyl-3-naphthylcarbonyl-2,4-dioxoimidazolidinyl) acetate (479 mg) was dissolved in a 20% trifluoroacetic acid/dichloromethane solution (10 mL), and the mixture was stirred at room temperature overnight. After 0.5N hydrochloric acid was added, and the solution was extracted twice using chloroform (100 mL). The resulting organic layer was washed with a saturated brine, and dried over anhydrous magnesium sulfate, and the solvent was distilled off. Further recrystallization from IPE afforded 396 mg of white crystals.

$^1$H-NMR (CDCl$_3$) δ1.47 (6H, s), 4.05 (2H, s), 7.48–7.65 (3H, m), 7.77 (1H, dd, J=8.3, 1.2 Hz), 7.90 (1H, d, J=7.6 Hz), 8.06 (1H, d, J=8.2 Hz), 8.48 (1H, d, J=8.4 Hz).

$^{13}$C-NMR (CDCl$_3$) δ25.0, 40.5, 62.0, 124.4, 124.7, 126.8, 128.6, 128.8, 129.6, 130.1, 130.8, 133.7, 134.4, 152.3, 165.9, 171.8, 173.7.

EXAMPLE 16

5-Methyl-3-naphthylcarbonyl-2,4-dioxo-5-phenylimidazolidinylacetic acid (Compound 16)

Tert-butyl (5-methyl-3-naphthylcarbonyl-2,4-dioxo-5-phenylimidazolidinyl acetate (400 mg) was dissolved in a 20% trifluoroacetic acid/dichloromethane solution (10 mL), and the mixture was stirred at room temperature overnight. After 0.5N hydrochloric acid was added, and the solution was extracted twice using chloroform (100 mL). The resulting organic layer was washed with a saturated brine, and dried over anhydrous magnesium sulfate, and the solvent was distilled off. Further recrystallization from IPE afforded 276 mg of white crystals.

$^1$H-NMR (CDCl$_3$) δ1.96 (3H, s), 3.61 (1H, d, J=18.2 Hz), 4.44 (1H, d, J=18.2 Hz), 7.39–7.62 (8H, m), 7.75 (1H, dd, J=7.1, 1.1 Hz), 7.90 (1H, d, J=7.6 Hz), 8.06 (1H, d, J=8.1 Hz), 8.45 (1H, d, J=8.1 Hz).

$^{13}$C-NMR (CDCl$_3$) δ21.0, 41.6, 67.4, 124.4, 124.7, 126.0, 126.8, 128.5, 128.8, 129.2, 129.5, 129.6, 130.1, 130.7, 133.7, 134.4, 135.7, 152.9, 165.7, 171.5, 171.9.

EXAMPLE 17

5,5-Dimethyl-3-(2-naphthylsulfonyl)imidazolidine-2,4-dione (Compound 17)

1.28 g of 5,5-dimethylimidazolidine-2,4-dione was dissolved in tetrahydrofuran (20 mL), and sodium hydride (60%, in oil) (0.25 g) was added at 0° C. under ice-cooling. After stirred for 30 minutes, 2-naphthalenesulfonyl chloride (2.38 g) was added at 0° C., and the mixture was stirred at room temperature overnight. After the solvent was distilled off, ethyl acetate (150 mL) was added to the reaction solution, and washed with 1N hydrochloric acid, an aqueous saturated sodium bicarbonate solution and a saturated brine in turn. The solution was dried over anhydrous magnesium sulfate, and the solvent was distilled off. Further purification by silica gel chromatography (hexane:ethyl acetate=2:1) afforded white crystals. The resulting fraction was recrystallized from IPE to obtain 232 mg of white crystals.

$^1$H-NMR (CDCl$_3$) δ1.41 (6H, s), 6.01 (1H, brs), 7.62–7.73 (2H, m), 7.92–8.09 (4H, m), 8.73 (1H, s).

$^{13}$C-NMR (CDCl$_3$) δ25.2, 59.0, 122.3, 127.9, 128.0, 129.7, 129.8, 130.0, 130.8, 131.9, 134.6, 135.8, 150.4, 172.3.

EXAMPLE 18

5,5-Dimethyl-3-naphthylsulfonyl imidazolidine-2,4-dione (Compound 18)

5,5-Dimethylimidazolidine-2,4-dione (1.28 g) was dissolved in tetrahydrofuran (20 mL), and sodium hydride (60%, in oil) (0.25 g) was added at 0° C. under ice-cooling. After stirred for 30 minutes, 1-naphthalene sulfonyl chloride (2.38 g) was added at 0° C., and the mixture was stirred at room temperature overnight. After the solvent was distilled off, 150 mL of ethyl acetate was added to the reaction solution, and the solution was washed with 1N hydrochloric acid, an aqueous saturated sodium bicarbonate solution and a saturated brine in turn. The solution was dried over anhydrous magnesium sulfate, and the solvent was distilled off. Further purification by silica gel chromatography (hexane:ethyl acetate=2:1) afforded 369 mg of white crystals.

$^1$H-NMR (CDCl$_3$) δ1.34 (6H, s), 6.24 (1H, brs), 7.58–7.72 (3H, m), 7.97 (2H, d, J=7.6 Hz), 8.17 (2H, d, J=8.1 Hz), 8.53 (1H, dd, J=8.4, 1.2 Hz), 8.70 (1H, d, J=8.1 Hz).

$^{13}$C-NMR (CDCl$_3$) δ25.1, 59.0, 123.2, 124.1, 127.3, 128.4, 129.3, 129.4, 132.3, 133.0, 134.0, 136.5, 150.6, 172.7.

EXAMPLE 19

5-Methyl-3-(2-naphthylsulfonyl)-5-phenyl imidazolidine-2,4-dione (Compound 19)

5-Methyl-5-phenylimidazolidine-2,4-dione potassium salt (1.00 g) was suspended in tetrahydrofuran (10 mL), 2-naphthalenesulfonyl chloride (1.02 g) was added slowly, and the mixture was stirred at room temperature overnight. After the solvent was distilled off, ethyl acetate (100 mL) was added to the reaction solution, and the solution was washed with 1N hydrochloric acid, an aqueous saturated sodium bicarbonate solution and a saturated brine in turn. The organic layer was dried over anhydrous magnesium sulfate, and the solvent was distilled off. Further purification by silica gel chromatography (hexane:ethyl acetate=2:1) afforded 242 mg of white crystals.

$^1$H-NMR (CDCl$_3$) δ1.74 (3H, s), 7.30–7.41 (6H, m), 7.63–7.74 (2H, m), 7.92–8.05 (4H, m), 8.71 (1H, brs).

$^{13}$C-NMR (CDCl$_3$) δ25.4, 63.6, 122.3, 125.2, 128.0, 128.0, 128.8, 129.0, 129.8, 129.9, 130.0, 130.8, 131.9, 134.6, 135.9, 137.8, 151.0, 171.0.

EXAMPLE 20

1-Benzyl-3-naphthylcarbonyl-5,5-diphenylimidazolidine-2,4-dione (Compound 20)

3-Naphthylcarbonyl-5,5-diphenylimidazolidine-2,4-dione (200 mg) was dissolved in DMF (2 mL), benzyl bromide (45 mg) was added, and potassium carbonate (36 mg) was further added. The reaction solution was stirred at room temperature overnight. Ethyl acetate (100 mL) was added to the reaction solution, and the solution was washed with 1N hydrochloric acid, an aqueous saturated sodium bicarbonate solution and a saturated brine in turn. After the solution was dried over anhydrous magnesium sulfate, and the solvent was distilled off. The resulting residue was recrystallized from IPE to obtain 55 mg of white crystals.

$^1$H-NMR (CDCl$_3$) δ4.58 (2H, s), 6.75 (1H, d, J=7.6 Hz), 6.99–7.10 (3H, m), 7.33–7.45 (11H, m), 7.52–7.55 (2H, m), 7.62 (1H, d, J=7.3 Hz), 7.87–7.90 (1H, m), 8.04 (1H, d, J=7.9 Hz), 8.38–8.41 (1H, m).

$^{13}$C-NMR (CDCl$_3$) δ45.6, 75.5, 124.4, 124.6, 126.7, 127.2, 128.1, 128.2, 128.4, 128.8, 128.8, 128.9, 129.3, 129.9, 129.9, 130.7, 133.7, 134.3, 135.9, 136.2, 152.9, 166.0, 171.2.

EXAMPLE 21

3-Naphthylcarbonyl-1-(2-oxo-2-phenylethyl)-5,5-diphenylimidazolidine-2,4-dione (Compound 21)

3-Naphthylcarbonyl-5,5-diphenylimidazolidine-2,4-dione (100 mg) was dissolved in DMF (2 mL), 2-bromoacetophenone (52 mg) was added, and potassium carbonate (36 mg) was further added. The reaction solution was stirred at room temperature overnight. Ethyl acetate (100 mL) was added to the reaction solution, and the solution was washed with 1N hydrochloric acid, an aqueous saturated sodium bicarbonate solution and a saturated brine in turn. After the solution was dried over anhydrous magnesium sulfate, the solvent was distilled off. The resulting residue was recrystallized from IPE to obtain 69 mg of white crystals.

$^1$H-NMR (CDCl$_3$+CD$_3$OD) δ4.79 (2H, s), 7.26–7.42 (12H, m), 7.48–7.64 (6H, m), 7.90 (2H, dt, J=7.2, 1.2 Hz), 8.08 (1H, d, J=8.2 Hz), 8.50 (1H, dd, J=8.8, 1.3 Hz).

$^{13}$C-NMR (CDCl$_3$+CD$_3$OD) δ47.2, 75.1, 124.5, 124.9, 126.8, 127.5, 128.5, 128.6, 128.7, 128.9, 129.3, 129.8, 130.2, 130.8, 133.5, 133.7, 134.3, 136.4, 152.9, 165.8, 176.0, 190.0.

EXAMPLE 22

1-Methyl-3-naphthylcarbonyl-5,5-diphenylimidazolidine-2,4-dione (Compound 22)

3-Naphthylcarbonyl-5,5-diphenylimidazolidine-2,4-dione (100 mg) was dissolved in DMF (4 mL), and sodium hydride (60%, in oil) (10 mg) was added at 0° C. under ice-cooling. After stirred for 30 minutes, methyl iodide (37 mg) was added at 0° C., and the mixture was stirred at room temperature overnight. Water (100 mL) was added to the reaction solution, and separated out white precipitates were filtered. Further recrystallization using hexane:ethyl acetate=1:1 afforded 64 mg of white crystals.

$^1$H-NMR (CDCl$_3$) δ2.83 (3H, s), 7.34–7.41 (5H, m), 7.43–7.49 (6H, m), 7.52–7.61 (2H, m), 7.69 (1H, dd, J=8.3, 1.2 Hz), 7.89–7.92 (1H, m), 8.06 (1H, d, J=8.2 Hz), 8.42–8.45 (1H, m).

$^{13}$C-NMR (CDCl$_3$) δ26.9, 74.6, 124.4, 124.7, 126.8, 128.4, 128.4, 128.8, 129.0, 129.3, 129.8, 130.0, 130.7, 133.7, 134.2, 135.9, 152.5, 166.0, 171.1.

EXAMPLE 23

1-Isobutyl-3-naphthylcarbonyl-5,5-diphenylimidazolidine-2,4-dione (Compound 23)

3-Naphthylcarbonyl-5,5-diphenylimidazolidine-2,4-dione (51 mg) was dissolved in DMF (0.4 mL), and sodium hydride (60%, in oil) (5 mg) was added. Then, methylisobutyl iodide (23 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 20 mg of white crystals.

$^1$H-NMR (CDCl$_3$) δ0.55 (6H, d, J=6.7 Hz), 0.92–1.02 (1H, m), 3.25 (2H, d, J=7.6 Hz), 7.26–7.61 (14H, m), 7.88 (1H, dd, J=6.1, 3.4 Hz), 8.02 (1H, d, J=8.4 Hz), 8.38 (1H, dd, J=6.2, 3.7 Hz).

$^{13}$C-NMR (CDCl$_3$) δ20.0, 27.4, 49.3, 75.4, 124.4, 124.7, 126.7, 126.8, 128.3, 128.6, 128.7, 128.8, 129.0, 129.0, 129.4, 129.7, 133.7, 134.1, 136.8, 152.8, 166.1, 171.1.

EXAMPLE 24

1-(4-Fluorobenzyl)-5-methyl-3-naphthylcarbonyl-5-phenylimidazolidine-2,4-dione (Compound 24)

5-Methyl-3-naphthylcarbonyl-5-phenylimidazolidine-2,4-dione (43 mg) was dissolved in DMF (0.4 mL), and sodium hydride (60%, in oil) (5 mg) was added. Then, 4-fluorobenzyl bromide (24 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 38 mg of white crystals.

$^1$H-NMR (CDCl$_3$) δ1.72 (3H, s), 3.91 (1H, d, J=15.4 Hz), 4.91 (1H, d, J=15.4 Hz), 6.92–7.00 (2H, m), 7.17–7.21 (2H, m), 7.32–7.62 (8H, m), 7.72 (1H, dd, J=7.3, 1.2 Hz), 7.89 (1H, dd, J=6.8, 1.8 Hz), 8.05 (1H, d, J=8.2 Hz), 8.47 (1H, dd, J=7.5, 1.2 Hz).

$^{13}$C-NMR (CDCl$_3$) δ21.7, 43.8, 67.6, 115.4, 115.7, 124.4, 124.6, 126.2, 126.8, 128.5, 128.8, 129.2, 129.3, 129.8, 130.1, 130.2, 130.7, 132.6, 132.7, 133.7, 134.3, 135.8, 153.1, 160.7, 164.0, 166.1, 171.8.

EXAMPLE 25

1-(3-Chlorobenzyl)-5-methyl-3-naphthylcarbonyl-5-phenylimidazolidine-2,4-dione (Compound 25)

5-Methyl-3-naphthylcarbonyl-5-phenylimidazolidine-2,4-dione (43 mg) was dissolved in DMF (0.4 mL), and sodium hydride (60%, in oil) (5 mg) was added. Then, 3-chlorobenzyl bromide (26 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 26 mg of white crystals.

$^1$H-NMR (CDCl$_3$) δ1.74 (3H, s), 3.90 (1H, d, J=15.6 Hz), 4.91 (1H, d, J=15.6 Hz), 7.11–7.28 (4H, m), 7.34–7.64 (8H, m), 7.74 (1H, dd, J=7.3, 1.2 Hz), 7.91 (1H, d, J=7.4 Hz), 8.07 (1H, d, J=8.2 Hz), 8.46 (1H, d, J=8.4 Hz).

¹³C-NMR (CDCl₃) δ21.7, 43.9, 67.6, 124.4, 124.6, 126.2, 126.5, 126.8, 128.1, 128.3, 128.5, 128.8, 129.2, 129.4, 129.5, 129.9, 130.0, 130.7, 133.7, 134.3, 134.5, 135.7, 138.8, 153.1, 166.0, 171.8.

EXAMPLE 26

5-Methyl-3-naphthylcarbonyl-1-(2-oxo-2-phenylethyl)-5-phenylimidazolidine-2,4-dione (Compound 26)

5-Methyl-3-naphthylcarbonyl-5-phenylimidazolidine-2,4-dione (43 mg) was dissolved in DMF (0.4 mL), and sodium hydride (60%, in oil) (5 mg) was added. Then, 25 mg of 2-bromoacetophenone was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 33 mg of white crystals.

¹H-NMR (CDCl₃) δ1.94 (3H, s), 4.20 (1H, d, J=18.0 Hz), 5.13 (1H, d, J=18.0 Hz), 7.39–7.65 (11H, m), 7.84–7.91 (4H, m), 8.06 (1H, d, J=8.2 Hz), 8.49 (1H, d, J=8.4 Hz).

¹³C-NMR (CDCl₃) δ21.1, 46.9, 67.5, 124.5, 124.8, 126.2, 126.7, 128.0, 128.5, 128.7, 128.9, 129.4, 129.5, 129.8, 130.0, 130.8, 133.7, 134.1, 134.2, 134.4, 136.4, 152.9, 165.8, 171.9, 191.7.

EXAMPLE 27

4-(5,5-Dimethyl-3-naphthylcarbonyl-2,4-dioxoimidazolidinylmethyl)benzonitrile (Compound 27)

5,5-Dimethyl-3-naphthylcarbonylimidazolidine -2,4-dione (35 mg) was dissolved in DMF (0.4 mL) and sodium hydride (60%, in oil) (5 mg) was added. Then, 4-cyanobenzyl bromide (25 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 24 mg of white crystals.

¹H-NMR (CDCl₃) δ1.92 (6H, s), 4.60 (2H, s), 7.34 (2H, dt, J=8.2, 1.7 Hz), 7.42–7.54 (5H, m), 7.56 (2H, dt, J=8.1, 1.7 Hz), 7.76 (1H, dd, J=7.3, 1.5 Hz), 7.88–8.00 (2H, m).

¹³C-NMR (CDCl₃) δ22.7, 42.1, 64.3, 123.5, 124.7, 124.7, 126.4, 127.3, 128.7, 128.8, 129.2, 129.6, 130.6, 130.8, 132.6, 133.2, 133.4, 140.0, 151.9, 168.2, 174.8.

EXAMPLE 28

1-(3-Chlorobenzyl)-5,5-dimethyl-3-naphthylcarbonylimidazolidine-2,4-dione (Compound 28)

5,5-Dimethyl-3-naphthylcarbonylimidazolidine-2,4-dione (35 mg) was dissolved in DMF (0.4 mL), and sodium hydride (60%, in oil) (5 mg) was added. Then, 3-chlorobenzyl bromide (26 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 14 mg of white crystals.

¹H-NMR (CDCl₃) δ1.92 (6H, s), 4.54 (2H, s), 7.14 (1H, dt, J=7.1, 1.7 Hz), 7.19 (1H, dd, J=7.6, 0.6 Hz), 7.23–7.27 (2H, m), 7.44–7.55 (4H, m), 7.76–7.80 (1H, m), 7.89–7.93 (1H, m), 7.98 (1H, dd, J=8.0, 0.5 Hz).

¹³C-NMR (CDCl₃) δ22.7, 42.1, 64.2, 123.5, 124.7, 124.8, 126.4, 126.6, 127.4, 128.5, 128.5, 128.8, 129.7, 130.1, 130.8, 133.3, 133.6, 134.6, 136.9, 152.0, 168.3, 174.8.

EXAMPLE 29

1-(4-Chlorobenzyl)-5,5-dimethyl-3-naphthylcarbonylimidazolidine-2,4-dione (Compound 29)

5,5-Dimethyl-3-naphthylcarbonylimidazolidine-2,4-dione (35 mg) was dissolved in DMF (0.4 mL), and sodium hydride (60%, in oil) (5 mg) was added. Then, 4-chlorobenzyl bromide (26 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 20 mg of white crystals.

¹H-NMR (CDCl₃) δ1.90 (6H, s), 4.53 (2H, s), 7.18–7.26 (4H, m), 7.42–7.55 (4H, m), 7.76 (1H, dd, J=8.1, 0.8 Hz), 7.90 (1H, d, J=7.8 Hz), 7.97 (1H, d, J=8.1 Hz).

¹³C-NMR (CDCl₃) δ22.7, 42.0, 64.2, 123.6, 124.7, 124.8, 126.4, 127.3, 128.8, 129.0, 129.6, 130.1, 130.7, 133.2, 133.6, 133.7, 134.3, 152.0, 168.3, 174.8.

EXAMPLE 30

5,5-Dimethyl-3-naphthylcarbonyl-1-(2-oxo-2-phenylethyl)imidazolidine-2,4-dione (Compound 30)

5,5-Dimethyl-3-naphthylcarbonylimidazolidine-2,4-dione (35 mg) was dissolved in DMF (0.4 mL), and sodium hydride (60%, in oil) (5 mg) was added. Then, 2-bromoacetophenone (25 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 7 mg of white crystals.

¹H-NMR (CDCl₃) δ2.04 (6H, s), 4.84 (2H, s), 7.42–7.61 (7H, m), 7.83–7.95 (5H, m).

¹³C-NMR (CDCl₃) δ22.7, 44.8, 64.8, 123.8, 124.7, 124.7, 126.4, 127.4, 128.0, 128.6, 128.9, 129.6, 130.6, 133.2, 133.6, 133.9, 134.2, 152.2, 168.4, 175.2, 189.7.

EXAMPLE 31

5,5-Dimethyl-3-naphthylcarbonyl-1-(2-oxo-2-p-tolylethyl)imidazolidine-2,4-dione (Compound 31)

5,5-Dimethyl-3-naphthylcarbonylimidazolidine-2,4-dione (35 mg) was dissolved in DMF (0.4 mL), and sodium hydride (60%, in oil) (5 mg) was added. Then, 2-bromo-4-methylacetophenone (27 mg) was added, and the mixture was stirred at room temperature overnight. Ethyl acetate (9.5 mL) was added to the reaction solution, separated out white precipitates were filtered, and the filtrate was concentrated and purified by silica gel chromatography (hexane:ethyl acetate=2:1) to obtain 12 mg of white crystals.

¹H-NMR (CDCl₃) δ2.04 (6H, s), 2.39 (3H, s), 4.81 (2H, s), 7.23 (2H, dd, J=8.6, 0.7 Hz), 7.46–7.55 (3H, m), 7.56 (1H, dd, J==7.8, 1.5 Hz), 7.74 (2H, dt, J=8.2, 1.8 Hz), 7.84–7.95 (3H, m).

¹³C-NMR (CDCl₃) δ21.8, 22.8, 44.7, 64.7, 123.8, 124.7, 124.7, 126.4, 127.4, 128.1, 128.6, 129.6, 129.6, 130.6, 131.5, 133.2, 133.7, 145.3, 152.2, 168.4, 175.2, 189.2.

EXAMPLE 32

1-(2-(4-Methoxyphenyl)-2-oxoethyl)-5,5-dimethyl-3-naphthylcarbonylimidazolidine-2,4-dione (Compound 32)

5,5-Diemthyl-3-naphthylcarbonylimidazolidine-2,4-dione (35 mg) was dissolved in DMF (0.4 mL), and sodium hydride (60%, in oil) (5 mg) was added. Then, 30 mg of 2-bromo-4-methoxyacetophenone was added, and the mixture was stirred at room temperature overnight. Ethyl acetate was (9.5 mL) was added to the reaction solution, separated out white precipitates were filtered, and the filtrate was concentrated and purified by silica gel chromatography (hexane:ethyl acetate=2:1) to obtain 11 mg of white crystals.

$^1$H-NMR (CDCl$_3$) δ2.04 (6H, s), 3.85 (3H, s), 4.79 (2H, s), 6.90 (2H, dt, J=8.9, 2.0 Hz), 7.46–7.58 (4H, m), 7.80–7.95 (5H, m).

$^{13}$C-NMR (CDCl$_3$) δ22.8, 44.5, 55.5, 64.7, 114.1, 123.8, 124.7, 124.7, 126.3, 127.0, 127.4, 128.6, 129.7, 130.3, 130.6, 133.2, 133.7, 152.3, 164.3, 168.4, 175.3, 188.0.

EXAMPLE 33

5,5-Dimethyl-1,3-bisnaphthylcarbonyl imidazolidine-2,4-dione (Compound 33)

5,5-Dimethylimidazolidine-2,4-dione (1.28 g) was dissolved in tetrahydrofuran (50 mL), and sodium hydride (60%, in oil) (0.80 g) was added at 0° C. under ice-cooling. After stirred for 30 minutes, 1-naphthoyl chloride (3.80 g) was added at 0° C., and the mixture was stirred at room temperature overnight. Ethyl acetate (200 mL) was added to the reaction solution, the mixture was washed with a saturated brine, and dried over anhydrous magnesium sulfate, and the solvent was distilled off. Further purification by silica gel chromatography (hexane:ethyl acetate=2:1) afforded 1.19 g of white crystals.

$^1$H-NMR (CDCl$_3$) δ2.06 (6H, s), 7.41–7.65 (7H, m), 7.72 (1H, dd, J=7.3, 1.1 Hz), 7.84–7.92 (4H, m), 8.04 (1H, d, J=8.2 Hz), 8.54 (1H, d, J=8.5, 0.8 Hz).

$^{13}$C-NMR (CDCl$_3$) δ23.1, 64.4, 123.69, 124.5, 124.6, 124.7, 125.0, 126.4, 127.0, 127.4, 128.3, 128.8, 128.8, 129.0, 129.6, 130.9, 130.9, 131.1, 133.0, 133.3, 133.8, 135.5, 149.4, 164.8, 168.6, 172.7.

EXAMPLE 34

3-Naphthylcarbonyl-1,3-diazaspiro[4.5]decane-2,4-dione (Compound 34)

5,5-Pentamethylenehydantoin (2.00 g) was dissolved in tetrahydrofuran (10 mL), and sodium hydride (60%, in oil) (0.49 g) was added at 0° C. under ice-cooling. After stirred for 30 minutes, 1-naphthoyl chloride (2.33 g) was added at 0° C., and the mixture was stirred at room temperature overnight. After the solvent was distilled off, ethyl acetate (100 mL) was added to the reaction solution, and the solution was washed with 1N hydrochloric acid, an aqueous saturated sodium bicarbonate solution and a saturated brine in turn. After drying over anhydrous magnesium sulfate, the solvent was distilled off to obtain the white solid. Further recrystallization with IPE and ethyl acetate afforded 1.87 g of white crystals.

$^1$H-NMR (CDCl$_3$) δ1.24–1.35 (3H, m), 1.55–1.93 (7H, m), 7.00 (1H, brs), 7.47–7.65 (3H, m), 7.72 (1H, dd, J=7.3, 1.2 Hz), 7.91 (1H, dd, J=8.8, 1.7 Hz), 8.06 (1H, d, J=8.2 Hz), 8.43–8.47 (1H, m).

$^{13}$C-NMR (CDCl$_3$) δ21.4, 24.3, 33.7, 61.8, 124.3, 124.7, 126.8, 128.4, 128.7, 129.6, 130.2, 130.7, 133.7, 134.0, 153.2, 166.3, 174.1.

EXAMPLE 35

5,5-Dimethyl-1,3-bis-(2-naphthylsulfonyl) imidazolidine-2,4-dione (Compound 35)

5,5-Dimethylimidazolidine-2,4-dione (1.28 g) was dissolved in tetrahydrofuran (20 mL), and sodium hydride (60%, in oil) (0.25 g) was added at 0° C. under ice-cooling. After stirred for 30 minutes, 2-naphthalenesulfonyl chloride (2.38 g) was added at 0° C., and the mixture was stirred at room temperature overnight. After the solvent was distilled off, ethyl acetate (150 mL) was added to the reaction solution, and the solution was washed with 1N hydrochloric acid, an aqueous saturated sodium bicarbonate solution and a saturated brine in turn. After drying over anhydrous magnesium sulfate, the solvent was distilled off. Further purification by silica gel chromatography (hexane:ethyl acetate=2:1) afforded 597 mg of white crystals.

$^1$H-NMR (CDCl$_3$) δ1.81 (6H, s), 7.62–7.75 (4H, m), 7.91–8.04 (8H, m), 8.68 (1H, s), 8.69 (1H, s).

$^{13}$C-NMR (CDCl$_3$) δ25.2, 59.0, 122.2, 122.6, 127.9, 127.9, 128.0, 128.1, 129.5, 129.9, 129.9, 130.0, 130.3, 131.4, 131.6, 131.8, 133.6, 134.5, 135.7, 136.0, 150.4, 172.3.

EXAMPLE 36

5,5-Dimethyl-1,3-bisnaphthylsulfonyl imidazolidine-2,4-dione (Compound 36)

5,5-Dimethylimidazolidine-2,4-dione (1.28 g) was dissolved in tetrahydrofuran (20 mL), and sodium hydride (60%, in oil) (0.25 g) was added at 0° C. under ice-cooling. After stirred for 30 minutes, 1-naphthalenesulfonyl chloride (2.38 g) was added at 0° C., and the mixture was stirred at room temperature overnight. After the solvent was distilled off, ethyl acetate (150 mL) was added to the reaction solution, and the mixture was washed with 1N hydrochloric acid, an aqueous saturated sodium bicarbonate solution and a saturated brine in turn. After drying over anhydrous magnesium sulfate, the solvent was distilled off. Further purification by silica gel chromatography (hexane:ethyl acetate=2:1) afforded 160 mg of white crystals.

$^1$H-NMR (CDCl$_3$) δ1.78 (6H, s), 7.46–7.64 (6H, m), 7.92–7.99 (2H, m), 8.15 (2H, t, J=8.5 Hz), 8.41–8.50 (3H, m), 8.59–8.64 (1H, m).

$^{13}$C-NMR (CDCl$_3$) δ24.4, 66.8, 122.8, 123.3, 124.1, 124.3, 127.1, 127.4, 128.1, 128.2, 128.7, 129.4, 129.5, 129.5, 131.4, 132.7, 133.5, 133.8, 133.9, 134.0, 136.6, 137.0, 147.2, 170.2.

EXAMPLE 37

5-Methyl-1,3-bis-(2-naphthylsulfonyl)-5-phenylimidazolidine-2,4-dione (Compound 37)

5-Methyl-5-phenylimidazolidine-2,4-dione potassium salt (1.00 g) was suspended in tetrahydrofuran (10 mL), 2-naphthalenesulfonyl chloride (1.02 g) was added slowly, and the mixture was stirred at room temperature overnight. After the solvent was distilled off, ethyl acetate (100 mL) was added to the reaction solution, and the mixture was washed with 1N hydrochloric acid, an aqueous saturated sodium bicarbonate solution and a saturated brine in turn.

The organic layer was dried over anhydrous magnesium sulfate, and the solvent was distilled off. Further purification by silica gel chromatography (hexane:ethyl acetate=2:1) afforded 242 mg of white crystals.

$^1$H-NMR (CDCl$_3$) δ2.25 (3H, s), 7.12–7.26 (4H, m), 7.36 (1H, t, J=7.5 Hz), 7.57–7.75 (5H, m), 7.81–8.02 (7H, m), 8.11 (1H, d, J=1.5 Hz), 8.69 (1H, d, J=0.6 Hz).

$^{13}$C-NMR (CDCl$_3$) δ21.9, 70.1, 122.2, 123.0, 126.3, 127.7, 127.9, 128.0, 128.1, 129.0, 129.1, 129.5, 129.9, 129.9, 130.0, 130.0, 130.3, 131.3, 131.4, 131.6, 131.8, 133.6, 134.4, 135.2, 135.6, 136.0, 147.4, 168.2.

Experiment 1

Chymase and Tryptase Inhibition Activity

Experimental Method

The chymase inhibition activity was measured according to the method of Kato et al. (J. Biochem., Vol.103, pp820 (1988)). That is, 72.5 μL of a solution adjusted so that the enzyme activity of recombinant human chymase (JP-A No.10-87567) became 2.3 μUnit with HEPES buffer, was added to 2.5 μL of a test substance dissolved in dimethyl sulfoxide (DMSO), a temperature was retained at 30° C. for 5 minutes, and 125 μL of 0.6 mM Suc-Ala-Ala-Pro-Phe-MCA (manufactured by Peptide Institute Inc.)/Tris buffer as a substrate was added to obtain a reaction solution. The reaction solution was set at a multi-well plate reader CYTOFLUOR Series 4000 (manufactured by Perceptive Biosystems), and a change in the fluorescent intensity was measured at 30° C. for 30 minutes with time (excitation wavelength 360 nm, detection wavelength 450 nm).

As a control, 2.5 μL of DMSO containing no test substance was used, and this was treated and measured similarly. As a blank, a Tris hydrochloric acid buffer was added instead of a chymase solution, and treated and measured similarly.

The chymase inhibition rate (%) was obtained by calculating a slope (S) of an approximation straight line for each test substance, a slope (C) of an approximation straight line for a control, a slope (Bs) of an approximation straight line for a blank of each test substance, and a slope (Bc) of approximation straight line for a blank of a control from a change in the fluorescent intensity, and calculating from the following equation.

Inhibition rate (%)=[1−(S−Bs)/(C−Bc)]×100

Then, the tryptase inhibition activity was measured according to the method of Muramatsu et al. (Biol. Chem. Hoppe-Seyler, vol.369, pp617(1988)). That is, 62.5 μL of a solution adjusted so that the enzyme activity of human lung tryptase (manufactured by Sigma) became 7.9 μUnit with 0.1M phosphate buffer-1.5M NaCl (pH7.1), was added to 2.5 μL of a test substance dissolved in DMSO, a temperature was retained at 30° C. for 5 minutes, and 125 μL of 0.6mM Boc-Val-Pro-Arg-MCA. HCl (manufactured by BACHEM)/0.1M phosphate buffer (pH7.1) as a substrate was added to obtain a reaction solution. The reaction solution was set at a multi-well plate reader CYTOFLUOR Series 4000 (manufactured by Perceptive Biosystems), and a change in the fluorescent intensity was measured at 30° C. for 30 minutes with time (excitation wavelength 360 nm, detection wavelength 450 nm). As a control, 2.5 μL of DMSO containing no test substance was used, and treated and measured similarly. As a blank, 0.1M phosphate buffer-1.5M NaCl (pH7.1) was added in place of a tryptase solution, and treated and measured similarly.

A tryptase inhibition rate (%) was obtained by calculating a slope (S) of an approximation straight line for each test material, a slope (C) of an approximation straight line for a control, a slope (Bs) of an approximation straight line for a blank of each test substance, and a slope (Bc) of an approximation straight line for a blank of a control from a change in the fluorescent intensity, and calculating from the following equation.

Inhibition rate (%)=[1−(S−Bs)/(C−Bc)]×100

Experimental Results

Regarding the compounds of the present invention, each 50% inhibition concentration (IC$_{50}$) was calculated from the chymase and tryptase inhibition activity obtained by the aforementioned method. The results are shown in Table 1. These results demonstrate that the compounds represented by the general formula (I) of the present invention have the chymase and/or tryptase inhibition activity.

TABLE 1

Human chymase and tryptase inhibition activity

| Test substance | Chymase IC$_{50}$ | Tryptase IC$_{50}$ |
| --- | --- | --- |
| Compound 1 | 6.6 × 10$^{-8}$ M | 3.9 × 10$^{-7}$ M |
| Compound 2 | 3.4 × 10$^{-7}$ M | 4.6 × 10$^{-8}$ M |
| Compound 3 | 1.0 × 10$^{-6}$ M | 9.3 × 10$^{-7}$ M |
| Compound 5 | 1.2 × 10$^{-6}$ M | 9.7 × 10$^{-7}$ M |
| Compound 7 | 6.5 × 10$^{-6}$ M | 3.7 × 10$^{-7}$ M |
| Compound 8 | 3.0 × 10$^{-5}$ M | 3.2 × 10$^{-6}$ M |
| Compound 9 | 7.3 × 10$^{-7}$ M | 1.0 × 10$^{-6}$ M |
| Compound 13 | 2.7 × 10$^{-6}$ M | 1.6 × 10$^{-6}$ M |
| Compound 14 | 2.6 × 10$^{-7}$ M | 1.6 × 10$^{-6}$ M |
| Compound 16 | 9.1 × 10$^{-7}$ M | 1.8 × 10$^{-6}$ M |
| Compound 22 | 3.5 × 10$^{-6}$ M | 8.9 × 10$^{-8}$ M |
| Compound 23 | 2.8 × 10$^{-7}$ M | 4.4 × 10$^{-6}$ M |
| Compound 25 | 5.8 × 10$^{-7}$ M | 8.6 × 10$^{-5}$ M |
| Compound 27 | 5.4 × 10$^{-7}$ M | 7.1 × 10$^{-6}$ M |
| Compound 28 | 2.2 × 10$^{-6}$ M | 2.2 × 10$^{-6}$ M |
| Compound 30 | 3.3 × 10$^{-6}$ M | 7.2 × 10$^{-6}$ M |
| Compound 33 | 1.8 × 10$^{-6}$ M | 1.5 × 10$^{-6}$ M |
| Compound 34 | 3.2 × 10$^{-5}$ M | 2.8 × 10$^{-7}$ M |

Experiment 2

Rat Mast Cell Histamine Release Inhibition Test

Experimental Method

A rat was killed by exsanguinations under ether anesthesia, and 30 mL of a buffer for mast cells (150 mM NaCl, 3.7 mM KCl, 3.0 mM Na$_2$HPO$_4$, 1 mM CaCl$_2$, 5.6 mM glucose) was injected intraperitoneally. An abdominal part was massaged for 90 seconds, and a suspension of intraperitoneal cell was taken. A suspension of an intraperitoneal cell collected from 5 animals was centrifuged at 100 G at 4° C. for 5 minutes, a buffer for mast cells was added, washed three times and, finally, adjusted so that the number of mast cells became 3 to 5×10$^5$ cells/mL (hereinafter, this solution is abbreviated as PEC).

Compound 5 was dissolved in DMSO to prepare a test drug solution at each concentration (final DMSO concentration 0.8%). 100 μL of the test drug solution was added to 400 μL of the prepared PEC, and pre-incubated at 37° C. for 15 minutes. After pre-incubation, each 50 μL of a solution of phosphatidylserine (10 μg/ml) and concanavalin A(15 μg/ml) which is a histamine-releasing substance was added, and further incubated for 20 minutes. 1.4 mL of an ice-cooled buffer for mast cells was added to stop the reaction, and centrifuged at 250 G at 4° C. for 10 minutes. An amount of the histamine supernatant was quantitated using a fluorescent method. That is, 20 μL of 1N NaOH was added to 40 μL of the supernatant, 20 μL of a 1% o-phthalaldehyde solution in methanol was further added, and allowed to stand at room temperature for 5 minutes. Thereafter, 20 μL of 3N hydrochloric acid was added, and the fluorescent intensity was measured at an excitation wavelength of 350 nm and a fluorescent wavelength of 450 nm to obtain an amount of histamine.

A histamine release inhibition rate (%) was calculated from the following equation:

Inhibition rate (%)=[1−(S−B)/(C−B)]×100

S: amount of histamine in the supernatant, C: amount of histamine in control, B: amount of histamine in blank Test Results

TABLE 2

Inhibition of release of histamine from mast cells

| Test drug concentration (μM) | Inhibition rate (%) |
|---|---|
| 100 | 83 |
| 80 | 78 |
| 40 | 59 |
| 8 | 28 |

As shown in Table 2, Compound 5 inhibited release of histamine concentration-dependently.

Preparation Example 1

| Tablet | |
|---|---|
| Compound 1 | 50 mg |
| Lactose | 80 mg |
| Starch | 17 mg |
| Magnesium stearate | 3 mg |
| Crystalline cellulose | 10 mg |

The above ingredients for one tablet are molded by the conventional method. This tablet may be coated with a sugar coating or a film (e.g. ethylcellulose etc.).

Preparation Example 2

| Capsule | |
|---|---|
| Compound 2 | 75 mg |
| Mannit | 75 mg |
| Starch | 17 mg |
| Calcium stearate | 3 mg |

The above ingredients for one capsule are uniformly mixed, granulated, and filled into a hard capsule by the conventional method. This granule to be filled may be coated with a sugar coating or a film (e.g. ethylcellulose etc.) as necessary.

Preparation Example 3

| Aqueous suspension eye drop | |
|---|---|
| Compound 9 | 0.5 g |
| Hydroxypropylmethylcellulose | 0.1 g |
| Sodium chloride | 0.9 g |
| Sodium dihydrogen phosphate dihydrate | 0.1 g |

| Aqueous suspension eye drop | |
|---|---|
| Benzalkonium chloride | 0.005 g |
| 0.1N sodium hydroxide | q.s. (pH7.2) |
| Purified water | Total 100 mL |

Hydroxypropylmethylcellulose is dispersed in about 80 mL of purified water by warming, and cooled to room temperature to dissolve it. To this solution are added sodium chloride, sodium dihydrogen phosphate dihydrate and benzalkonium chloride to dissolve them, and 0.1N sodium hydroxide is added to adjust to pH 7.2. To this solution is added Compound 1, and suspended uniformly with a homogenizer. Purified water is added to make a solution of total 100 mL, to prepare an aqueous suspension for an eye drop.

Industrial Applicability

Since the compound represented by the general formula (I) of the present invention or a pharmaceutically acceptable salt has the excellent chymase and/or tryptase inhibition activity, it is useful as an agent for preventing/treating various diseases associated with chymase and/or tryptase.

Some embodiments of the present invention have been explained in detail above. However, a person skilled in the art can variously modify or alter the shown particular embodiments without substantially departing from the novel teaching and advantages of the present invention, and such modification and alteration are all included in the scope of the spirit of the present invention claimed in claims below.

The present application is based on Japanese Patent Application No.2001-112373 which was filed in Japan, the entire contents of which are included in the present application.

What is claimed is:

1. A compound represented by the general formula (I):

wherein $R^1$ and $R^2$ are the same or different, and denote a lower alkyl group or a phenyl group, or $R^1$ and $R^2$ are taken together to form a ring, $R^3$ denotes an optionally substituted naphthyl group or heterocyclic group, A denotes oxygen or $NR^4$ wherein $R^4$ is hydrogen or optionally substituted lower alkyl group, or $NB^2R^5$ wherein $R^5$ is aryl group, and $B^2$ is carbonyl group or sulfonyl group, and $B^1$ denotes a carbonyl group or a sulfonyl group, or a pharmaceutically acceptable salt thereof.

2. The compound according to claim 1, wherein $R^1$ and $R^2$ are the same or different, and are a lower alkyl group or a phenyl group, $R^3$ is a furyl group or an optionally substituted naphthyl group, and A is oxygen or $NR^4$ wherein $R^4$ is hydrogen or optionally substituted lower alkyl group in the general formula (I), or the pharmaceutically acceptable salt thereof.

3. The compound according to claim 1, wherein $B^1$ and $B^2$ are a carbonyl group in the general formula (I), or the pharmaceutically acceptable salt thereof.

4. A medicament, which comprises the compound as defined in claim 1, or a pharmaceutically acceptable salt thereof.

5. A chymase and/or tryptase inhibiting agent, which comprises the compound as defined in claim 1, or a pharmaceutically acceptable salt thereof.

6. The medicament according to claim 4, which is an agent for treating diseases associated with chymase and/or tryptase.

7. The medicament according to claim 6, wherein the disease associated with chymase and/or tryptase is allergic, inflammatory or circulatory disease.

8. The medicament according to claim 6, wherein the disease associated with chymase is chorioretinopathy, glaucoma, myopia or asthenopia.

9. A pharmaceutical composition, which comprises the compound as defined in claim 1, or a pharmaceutically acceptable salt thereof.

10. A method of treating a disease associated with chymase and/or tryptase, which comprised administering an effective amount of the compound as defined in claim 1, or a pharmaceutically acceptable salt thereof to a warm-blooded animal, wherein the disease is selected from the group consisting of pancreatitis, ulcerative colitis, Crohn's disease, nephritis, hepatitis, bronchopneumonia, atopy, arthritis, rheumatism, keratoconjunctivitis, iridocyclitis, uveitis, orbital inflammation, vernal catarrh, allergic rhinitis, restenosis after circulatory disease, restenosis after blood vessel disorder due to percutaneous transluminal angioplasty, diabetic or non-diabetic renal disorder, peripheral circulatory disorder, itching associated with inflammatory or allergic disorder, chorioretinopathy, retinitis pigmentosa, macular degeneration, ischemic optic nerve disease, arteriovenous occulusion, diabetic retinopathy, choroidal disease following retinal lesion, glaucoma, myopia, asthenopia, thrombophlebitis, disseminated intravascular coagulation, psoriasis, scleroderma, interstitial pneumonia, pulmonary fibrosis, hepatic cirrhosis, periodontal disease and pterygium.

11. A method for manufacturing a chymase and/or tryptase inhibiting agent, which comprised mixing the compound of claim 1 or a pharmaceutically acceptable salt thereof with an excipient, binder, disintegrating agent, lubricant, absorption promoter, buffer, surfactant, solubilizer, preservative, emulsifier, isotonic or pH adjusting agent.

* * * * *